United States Patent [19]

Matsuda et al.

[11] Patent Number: 5,180,747
[45] Date of Patent: Jan. 19, 1993

[54] STABILIZED FAT-SOLUBLE VITAMIN COMPOSITIONS

[75] Inventors: Yoshihisa Matsuda, Kyoto; Reiko Teroaka, Osaka; Yukio Tanaka; Hisato Abe, both of Saitama, all of Japan

[73] Assignee: Nisshin Flour Milling Co., Ltd., Tokyo, Japan

[21] Appl. No.: 887,364

[22] Filed: May 21, 1992

Related U.S. Application Data

[63] Continuation of Ser. No. 483,533, Feb. 22, 1990, abandoned.

[30] Foreign Application Priority Data

Feb. 28, 1989 [JP] Japan .................................. 1-45358
Feb. 13, 1990 [JP] Japan .................................. 2-29778

[51] Int. Cl.$^5$ ...................... A61K 31/12; A61K 31/07
[52] U.S. Cl. .................... 514/681; 514/725; 514/972
[58] Field of Search ............... 514/681, 725, 972, 970

[56] References Cited

U.S. PATENT DOCUMENTS

| 2,980,588 | 4/1961 | Larde | 514/458 |
| 3,253,992 | 5/1966 | Brooks | 514/725 |
| 4,141,994 | 2/1979 | Aneja et al. | 514/547 |
| 4,826,828 | 5/1989 | Wilmott et al. | 514/725 |
| 4,840,970 | 6/1989 | Ohasi et al. | 514/690 |
| 4,929,774 | 5/1990 | Fukamachi et al. | 568/824 |

FOREIGN PATENT DOCUMENTS 129003 10/1984 European Pat. Off. .
4062 10/1967 Japan .
1375436 11/1974 United Kingdom .

*Primary Examiner*—Frederick E. Waddell
*Assistant Examiner*—Raymond J. Henley, III
*Attorney, Agent, or Firm*—Abelman Frayne & Schwab

[57] ABSTRACT

Stabilized fat-soluble vitamin compositions are disclosed which comprise fat-soluble vitamins and carotenoids as a stabilizer. They are stable to light and have a wide range of applications such as medicines, veterinary medicines, food additives, feed additives, nutrient supplements or the like.

8 Claims, No Drawings

STABILIZED FAT-SOLUBLE VITAMIN COMPOSITIONS

This is a continuation of application Ser. No. 07/483,533 filed on Feb. 22, 1990, now abandoned.

FIELD OF THE INVENTION

This invention relates to stabilized fat-soluble vitamin compositions which comprise fat-soluble vitamins and carotenoids as a stabilizer. The compositions of the invention have a wide range of applications such as medicines, veterinary medicines, food additives, feed additives, nutrient supplements or the like.

BACKGROUND OF THE INVENTION

Fat-soluble vitamins such as vitamin K, vitamin A, coenzyme Q and vitamin D are known to be unstable to light, etc. Thus various methods have been attempted to stabilize those fat-soluble vitamins in formulating pharmaceutical preparations.

For the stabilization of vitamin $K_1$ (phylloquinone) and vitamin $K_2$ (menaquinone) having hemostasis-enhancing action (called antihemorrhagic vitamins) which are known to be very unstable to light, attempts have been made wherein vitamin K dissolved in an oil and fat is encapsulated into a colored capsule for light shielding and wherein a variety of stabilizers are incorporated into vitamin K. Japanese Patent Publication No. 4062/1967 discloses a method for the stabilization of menadione (vitamin $K_3$) or its sodium bisulfite solution using as a stabilizer one or more of caffeine, theobromine, theophylline or their soluble salts.

Further, measures have been taken for pharmaceutical preparations of vitamin A or coenzyme Q, such as use of a variety of stabilizers or protection from light or oxygen by means of encapsulation.

However the above attempts have been accomplished with unsatisfactory results.

Thus the present invention results from efforts to develop a new stabilizer for fat-soluble vitamins.

DISCLOSURE OF THE INVENTION

According to the present invention, there are provided stabilized fat-soluble vitamin compositions which comprise fat-soluble vitamins and carotenoids as a stabilizer. Optionally, the compositions of the invention may further comprise oil components and other conventional additives.

One embodiment of the composition includes a solubilized solution which comprises fat-soluble vitamins, carotenoids, a solubilizing agent and water, optionally together with an oil component and other conventional additives.

Another embodiment of the composition includes an emulsion which comprises fat-soluble vitamins, carotenoids, an emulsifying agent and water, optionally together with an oil component and other conventional additives.

The fat-soluble vitamins which are stabilized include vitamin K such as vitamin $K_1$, vitamin $K_2$, vitamin $K_3$, vitamin $K_4$, vitamin $K_5$, vitamin $K_6$, vitamin $K_7$; vitamin A such as vitamin $A_1$, vitamin $A_1$ acetate, vitamin $A_2$, vitamin $A_3$, vitamin A acid; coenzymes Q such as $CoQ_7$, $CoQ_8$, $CoQ_9$ and $CoQ_{10}$; vitamin D such as vitamin $D_1$, vitamin $D_2$, vitamin $D_3$, vitamin $D_4$; activated vitamin D such as activated vitamins $D_2$, $D_3$ and $D_4$ and the like. Those fat-soluble vitamins, either alone or in combination, can be stabilized with the stabilizer.

The carotenoids which are used as the stabilizer in the invention can include α-carotene, β-carotene, γ-carotene, δ-carotene, lycopene, cryptxanthin, lutein, zeaxanthin, rhodoxanthin, canthaxanthin, capsanthin, crocetin, squalene, β-ionone and the like. Those carotenoids may be used either alone or in combination.

The carotenoids are added in an amount effective as the stabilizer for fat-soluble vitamins. Usually, they can be added in an amount of at least 0.01% by weight based on the fat-soluble vitamin. The maximum amount of the carotenoids added is not limited, but preferably is the upper limit of the solubility of the carotenoids in the resulting composition.

The compositions of the invention can be prepared by any methods which allow fat-soluble vitamins and carotenoids to be uniformly mixed, for example, by mixing them in an oil component, an organic solvent or the like. Alternatively, both fat-soluble vitamins and carotenoids which have been heat-melted may be mixed by stirring.

The oil components which are employed in the invention can include animal oils, vegetable oils, hydrocarbon oils and synthetic glyceride oils, examples of which include various fish oils such as sardin oil, saury oil, squid oil and herring oil; various vegetable oils such as soybean oil, rape oil, corn oil, corn germ oil, cottonseed oil, olive oil, sunflower oil and sesame oil; hydrocarbon oils such as n-hexane, fluid paraffin, squalane, Squalene-EX and Synthelane 30 manufactured by Nikko Chemical Co., Ltd.; and synthetic glycerides such as a medium-chain fatty acid triglyceride called MCT. The organic solvents used include known solvents.

The stabilized fat soluble vitamin compositions of the invention can be prepared by adding a stabilizing amount of carotenoids to the oil component in which fat-soluble vitamins have been dissolved and dissolving the mixture or by adding a desired amount of fat-soluble vitamins to the oil component in which carotenoids are dissolved and dissolving the mixture or by mixing three components simultaneously and dissolving the mixture. In this case any methods may be used which can prepare a uniform mixture. If necessary, pharmaceutically acceptable additives may be further added to the stabilized fat-soluble vitamin compositions.

The emulsifying agents which are employed in the preparation of the stabilized composition in the emulsion form include phospholipids such as yolk phospholipid, soybean phospholipid and modified phospholipids; glycerin fatty acid esters; polyglycerin fatty acid esters such as decaglycerin fatty acid esters; sorbitan fatty acid esters; polyethylene glycol fatty acid esters; polyoxyethylene sorbitan fatty acid esters; polyoxyethylene alkyl ethers; polyoxyethylene castor oil; polyoxyethylene hardened castor oil; polyoxyethylene sorbit fatty acid esters; and polyoxyethylene glycerin fatty acid esters. Phospholipids are preferred.

In the preparation of the stabilized composition in the form of the solubilized solution, the above emulsifying agents can be used as the solubilizing agents depending on the intended purpose.

The emulsion and the solubilized solution can be prepared by emulsifying or solubilizing the stabilized fat-soluble vitamin composition, for example using any stirring means.

The stabilized fat-soluble vitamin compositions of the present invention can be used in the suitable preparations. The preparations include liquid preparations such as injections, syrups; solid preparations such as tablets, granules, powders; semi-solid preparations such as creams, ointments; and capsules such as soft and hard capsules.

In forming the above preparations, pharmaceutically acceptable additives can be used, which include other stabilizers than carotenoids; fillers such as lactose, starch, crystalline cellulose, synthetic aluminum silicate; coloring agents such as tar dyes, titanium oxide, yellow iron oxide and red iron oxide; sweetening agents such as white sugar, sodium saccharin, D-xylose, sorbit and mannit; and flavoring agents such as aliphatic alcohols (e.g. peppermint oil), aromatic alcohols and aromatic aldehydes, or the like.

The stabilized fat-soluble vitamin compositions of the invention have high stability to light and do not exhibit reduction in activity even after a long storage. They have a wide range of applications such as medicines, veterinary medicines, food additives, feed additives, nutrient supplements or the like.

The invention is further illustrated by the following non-limitative examples.

EXAMPLE 1

25 mg of vitamin $K_2$ were added to 23 g of rape oil to prepare Control Sample I. To the above control sample was further added $\beta$-carotene in an amount of 0.125 mg, 0.25 mg, 1.25 mg and 2.5 mg to prepare Samples A, B, C and D, respectively.

Each of these samples was irradiated with a white fluorescent lamp at a distance of 30 cm from the light source to the surface of the sample under an illuminance of 2000 luces over a period of 8 hours.

An aliquot of the sample was removed at an interval of one hour during the irradiation and measured for percentage (%) of vitamin $K_2$ retained in the sample by high performance liquid chromatography.

The results are shown in Table 1.

TABLE 1

| Irradiation time (hr) | Sample | | | | Control Sample I |
|---|---|---|---|---|---|
| | A | B | C | D | |
| 1 | 95.47 | 94.80 | 98.17 | 97.62 | 87.39 |
| 2 | 91.53 | 89.68 | 97.22 | 96.26 | 77.76 |
| 3 | 85.22 | 85.95 | 94.13 | 95.31 | 69.11 |
| 4 | 79.79 | 82.69 | 92.80 | 93.83 | 61.93 |
| 5 | 75.10 | 79.42 | 90.64 | 93.60 | 55.50 |
| 6 | 71.17 | 76.34 | 88.75 | 92.93 | 50.58 |
| 7 | 67.70 | 73.25 | 86.81 | 90.84 | 46.04 |
| 8 | 64.34 | 70.21 | 83.47 | 91.03 | 41.68 |

EXAMPLE 2

25 mg of vitamin $K_2$ and 25 mg of vitamin $K_1$ were independently added to 25 ml of n-hexane to prepare Control Samples II and III, respectively. To each of the above control samples were further added 1.5 mg of $\beta$-carotene to prepare Samples E and F, respectively.

Each of these samples was irradiated in the same way as in Example 1 with a white fluorescent lamp under an illuminance of 2000 luces over a period of 8 hours.

An aliquot of the sample was removed at an interval of 1 hour during the irradiation and measured for percentage (%) of vitamin $K_2$ and vitamin $K_1$ respectively retained in the sample by high performance liquid chromatography.

The results are shown in Table 2.

TABLE 2

| Irradiation time (hr) | Sample | | | |
|---|---|---|---|---|
| | E | Control Sample II | F | Control Sample III |
| 1 | 96.54 | 88.38 | 96.25 | 94.24 |
| 2 | 94.78 | 80.35 | 94.94 | 88.98 |
| 3 | 92.15 | 72.63 | 96.20 | 82.56 |
| 4 | 91.36 | 66.02 | 94.98 | 77.60 |
| 5 | 89.54 | 62.20 | 92.40 | 72.75 |
| 6 | 88.80 | 58.86 | 90.80 | 68.82 |
| 7 | 88.49 | 54.83 | 91.17 | 64.08 |
| 8 | 86.85 | 51.33 | 90.06 | 61.70 |

EXAMPLE 3

25 mg of vitamin A acetate were added to 25 ml of n-hexane to prepare Control Sample IV. 2 mg and 4 mg of $\beta$-carotene, respectively were added to the above control sample to prepare Samples G and H, respectively.

Each of these samples was irradiated in the same way as in Example 1 with a white fluorescent lamp under an illuminance of 2000 luces over a period of 24 hours.

An aliquot of the sample was removed at intervals shown in the table below during the irradiation and measured for percentage (%) of vitamin A acetate retained in the sample by high performance liquid chromatography.

The results are shown in Table 3.

TABLE 3

| Irradiation time (hr) | Sample | | Control Sample IV |
|---|---|---|---|
| | G | H | |
| 2 | 97.54 | 98.31 | 97.28 |
| 4 | 95.39 | 96.83 | 90.13 |
| 6 | 92.71 | 93.69 | 89.04 |
| 8 | 91.40 | 90.76 | 84.58 |
| 15 | 81.80 | 83.82 | 68.86 |
| 24 | 73.02 | 74.72 | 56.71 |

EXAMPLE 4

25 mg of ubidecarenone ($CoQ_{10}$) were added to 25 ml of n-hexane to prepare Control Sample V. 0.775 mg of $\beta$-carotene was added to the above control sample to prepare Sample I.

Each of these samples was irradiated in the same way as in Example 1 with a white fluorescent lamp under an illuminance of 2000 luces over a period of 24 hours.

An aliquot of the sample was removed at intervals shown in the table below during the irradiation and measured for percentage (%) of ubidecarenone retained in the sample by high performance liquid chromatography.

The results are shown in Table 4.

TABLE 4

| Irradiation time (hr) | Sample | |
|---|---|---|
| | I | Control Sample V |
| 2 | 96.19 | 94.65 |
| 4 | 95.82 | 86.21 |
| 6 | 92.87 | 82.92 |
| 8 | 93.03 | 76.37 |
| 15 | 88.49 | 58.30 |

TABLE 4-continued

| Irradiation time (hr) | Sample I | Control Sample V |
|---|---|---|
| 24 | 83.12 | 48.42 |

EXAMPLE 5

25 mg of vitamin $K_2$ were added to 25 ml of n-hexane to prepare Control Sample VI. 1.58 mg of canthaxanthin and 1.5 mg of lycopen, respectively were added to the above control sample to prepare Samples J and K, respectively.

Each of these samples was irradiated in the same way as in Example 1 with a white fluorescent lamp under an illuminance of 2000 luces over a period of 8 hours.

An aliquot of the sample was removed at an interval of 1 hour during the irradiation and measured for percentage (%) of vitamin $K_2$ retained in the sample by high performance liquid chromatography.

The results are shown in Table 5.

TABLE 5

| Irradiation time (hr) | Sample J | K | Control Sample VI |
|---|---|---|---|
| 1 | 98.04 | 97.44 | 88.38 |
| 2 | 96.55 | 95.01 | 80.35 |
| 3 | 94.86 | 93.02 | 72.63 |
| 4 | 92.18 | 91.62 | 66.02 |
| 5 | 90.99 | 90.43 | 62.20 |
| 6 | 89.71 | 89.43 | 58.86 |
| 7 | 89.11 | 89.33 | 54.83 |
| 8 | 88.64 | 88.31 | 51.33 |

The above results indicate that canthaxanthin and lycopen are effective as a stabilizer to prevent light degradation of vitamin $K_2$.

EXAMPLE 6

25 mg of vitamin $K_2$ were added to 25 ml of n-hexane to prepare Control Sample VII. 0.3 mg of $\beta$-carotene, 0.316 mg of canthaxin, 0.3 mg of lycopen and 0.3 mg of $\gamma$-carotene, respectively were added to the above control sample to prepare Samples L, M, N and O, respectively.

Each of these samples was irradiated in the same way as in Example 1 with a white fluorescent lamp under an illuminance of 2000 luces over a period of 8 hours.

An aliquot of the sample was removed at an interval of 1 hour during the irradiation and measured for percentage (%) of vitamin $K_2$ retained in the sample by high performance liquid chromatography.

The results are shown in Table 6.

TABLE 6

| Irradiation time (hr) | Sample L | M | N | O | Control Sample VII |
|---|---|---|---|---|---|
| 1 | 95.22 | 97.40 | 99.90 | 97.12 | 88.38 |
| 2 | 91.94 | 93.26 | 94.98 | 92.40 | 80.35 |
| 3 | 90.72 | 91.19 | 92.73 | 90.20 | 72.63 |
| 4 | 86.86 | 88.48 | 90.19 | 87.58 | 66.02 |
| 5 | 84.77 | 85.40 | 87.65 | 85.71 | 62.20 |
| 6 | 81.86 | 85.39 | 85.19 | 83.86 | 58.86 |
| 7 | 79.62 | 81.79 | 84.86 | 82.59 | 54.83 |
| 8 | 78.36 | 79.27 | 79.44 | 80.67 | 51.33 |

EXAMPLE 7

Vitamin $K_1$, $\beta$-carotene and rape oil were mixed in such a proportion that one capsule contained 5 mg of vitamin $K_1$, 0.006 mg of $\beta$-carotene and 245 mg of rape oil. The resulting liquid mixture was encapsulated by a conventional method with gelatin coat to form soft capsules (Sample P). Separately, soft capsules (Control Sample VIII) were prepared from the same liquid mixture as above but containing no $\beta$-carotene.

These samples were irradiated with a white fluorescent lamp under an illuminance of 1000 luces and measured for percentage of vitamin $K_1$ retained in the sample.

The results are shown in Table 7.

TABLE 7

| Irradiation time (hr) | Sample P | Control Sample VIII |
|---|---|---|
| 6 | 101.8 | 97.4 |
| 30 | 100.8 | 82.2 |
| 120 | 96.4 | 27.4 |

EXAMPLE 8

5.0 g of vitamin $K_1$ and 0.126 g of $\beta$-carotene were dissolved in 50 ml of a mixed solvent (ethanol:chloroform=1:1) and to the solution were added 138 g of lactose, 101 g of Avicel and 8 g of PVP. The resulting mixture was kneaded, granulated, dried and graded to prepare granules as Sample Q.

Separately, the same granules as above but containing no $\beta$-carotene (Control Sample IX) were prepared in the same way as above.

These samples were irradiated with a white fluorescent lamp under an illuminance of 1000 luces and measured for percentage (%) of vitamin $K_1$ retained in the sample.

The results are shown in Table 8.

TABLE 8

| Irradiation time (hr) | Sample Q | Control Sample IX |
|---|---|---|
| 24 | 90.3 | 82.8 |
| 72 | 87.8 | 75.0 |
| 120 | 80.8 | 71.5 |

EXAMPLE 9

To 50 mg of vitamin $K_1$, 1 mg of $\beta$-carotene and 2000 mg of polyoxyethylene hardened castor oil (HCO-60 manufactured by Nikko Chemical Co., Ltd.) were added 300 ml of distilled water. The mixture was warmed with stirring to prepare a solubilized solution as Sample R.

Separately, the same solubilized solution as above but containing no $\beta$-carotene was prepared as Control Sample X.

The same procedure as mentioned above was repeated but substitution of vitamin $K_2$ for vitamin $K_1$ to prepare Sample S. The same solubilized solution as above but containing no $\beta$-carotene was prepared as Control Sample XI.

These samples were respectively placed in a transparent beaker and irradiated with a white fluorescent lamp under an illuminance of 2000 luces on the surface of the sample over a period of 6 hours.

An aliquot of the sample was removed at intervals shown in the table below during the irradiation and measured for percentage (%) of vitamin $K_1$ and vitamin $K_2$ retained in the sample.

The results are shown in Table 9.

TABLE 9

| Irradiation time (hr) | Sample | | | |
|---|---|---|---|---|
| | R | Control Sample X | S | Control Sample XI |
| 0.5 | 96.8 | 90.5 | 98.3 | 92.8 |
| 1 | 93.7 | 84.7 | 93.9 | 85.5 |
| 2 | 90.7 | 76.9 | 86.8 | 69.2 |
| 3 | 86.6 | 70.4 | 83.7 | 67.4 |
| 4 | 82.5 | 63.6 | 80.9 | 63.7 |
| 5 | 78.9 | 58.5 | 81.0 | 59.2 |
| 6 | 76.8 | 57.6 | 75.7 | 53.8 |

EXAMPLE 10

To distilled water were added 50 mg of vitamin $K_2$, 10.0 g of soybean oil, 1.2 g of soybean lecithin, 2.5 g of glycerin and 1 mg of $\beta$-carotene to a total volume of 300 ml. The mixture was emulsified to prepare a vitamin $K_2$-containing emulsion as Sample T.

Separately, the same emulsion as above but containing no $\beta$-carotene was prepared as Control Sample XII.

The same procedure as mentioned above was repeated but substitution of vitamin $K_1$ for vitamin $K_2$ to prepare Sample U. The same emulsion as above but containing no $\beta$-carotene was prepared as Control Sample XIII.

These samples were irradiated with a white fluorescent lamp under an illuminance of 2000 luces and measured for percentage (%) of vitamin $K_2$ and vitamin $K_1$ retained in the sample.

The results are shown in Table 10.

TABLE 10

| Irradiation time (hr) | Sample | | | |
|---|---|---|---|---|
| | T | Control Sample XII | U | Control Sample XIII |
| 0.5 | 99.8 | 90.2 | 99.3 | 93.7 |
| 1 | 98.7 | 86.2 | 97.9 | 90.3 |
| 2 | 97.4 | 79.1 | 96.5 | 84.6 |
| 3 | 94.6 | 72.3 | 94.8 | 78.9 |
| 4 | 92.5 | 71.8 | 94.4 | 74.5 |
| 5 | 92.5 | 68.1 | 91.5 | 69.6 |
| 6 | 86.9 | 62.4 | 90.7 | 65.7 |

The above results indicate that the presence of $\beta$-carotene in the vitamin $K_2$ or $K_1$-containing emulsion provides remarkably improved light stability of vitamin $K_2$ or $K_1$.

What is claimed is:

1. A method of providing light stabilization and inhibiting reduction in activity of a fat-soluble vitamin K composition, which comprises:
    preparing a fat-soluble vitamin K composition which includes a least 0.01% of vitamin K, by weight, and at least 0.01%, by weight, based on the weight of the vitamin, of a stabilizer selected from the group consisting of a $\alpha$-carotene, $\gamma$-carotene, lycopene and canthaxanthin.

2. The method of claim 1, wherein the fat-soluble vitamin K composition further comprises a pharmaceutically acceptable oil carrier and other conventional additives.

3. The method of claim 1, wherein the fat-soluble vitamin K composition is formulated into a solubilized solution.

4. The method of claim 1 wherein the fat-soluble vitamin K composition is formulated into an emulsion.

5. The method of claim 1, wherein the fat-soluble vitamin K composition is in the form of a semi-solid.

6. The method of claim 1, wherein the fat-soluble vitamin K composition is in the form of a solid.

7. The method of claim 1, wherein the vitamin K is vitamin $K_1$, vitamin $K_2$, vitamin $K_3$, vitamin $K_5$, vitamin $K_6$, or vitamin $K_7$.

8. The method of claim 2, wherein the oil carrier is animal, vegetable, hydrocarbon and synthetic glyceride oils.

* * * * *